United States Patent [19]
Wunderlich et al.

[11] Patent Number: 5,932,245
[45] Date of Patent: *Aug. 3, 1999

[54] GELATIN OR COLLAGEN HYDROLYSATE CONTAINING DRUG FORMULATION THAT PROVIDES FOR IMMEDIATE RELEASE OF NANOPARTICLE DRUG COMPOUNDS

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec Pharma GmbH, Heidelberg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/244,615
[22] PCT Filed: Dec. 4, 1992
[86] PCT No.: PCT/DE92/01010
§ 371 Date: Oct. 25, 1994
§ 102(e) Date: Oct. 25, 1994
[87] PCT Pub. No.: WO93/10768
PCT Pub. Date: Jun. 10, 1993

[30] Foreign Application Priority Data

Dec. 5, 1991 [DE] Germany .............................. 41 40 177
Dec. 5, 1991 [DE] Germany .............................. 41 40 178
Dec. 5, 1991 [DE] Germany .............................. 41 40 195

[51] Int. Cl.$^6$ ................. A61K 9/48; A61K 9/14
[52] U.S. Cl. .......................... 424/451; 424/456; 424/457; 424/468; 424/489; 424/490; 424/492; 424/464; 514/951; 514/962

[58] Field of Search ...................... 424/456, 451, 424/457, 468, 489, 490, 492, 464; 514/951, 962

[56] References Cited

U.S. PATENT DOCUMENTS

| | | | |
|---|---|---|---|
| 5,080,907 | 1/1992 | Iijima et al. | 424/469 |
| 5,118,528 | 6/1992 | Fessi et al. | 427/213.36 |
| 5,133,908 | 7/1992 | Stainmesse et al. | 264/4.1 |

*Primary Examiner*—Raj Bawa
*Attorney, Agent, or Firm*—Burns, Doane, Swecker & Mathis, L.L.P.

[57] ABSTRACT

Nanosols and process for preparing the same allow colloidally dispersed solutions of scarcely water-soluble active substances to be stabilized with gelatin or its derivatives, by partly or fully setting the iso-ionic point (IIP, equivalent to a neutral charge) between the gelatin and the surface charged active substance particles. In order to neutralize the charge of the system composed of active substance particles and gelatin, the surface charge of the particles is compensated by a corresponding opposite charge of the gelatin molecules. For that purpose, a determined charge in relation to the isoelectric point (IEP) and the pH value of the solution is set on the gelatin molecules. By stabilizing in this way the practically monodispersed state thus generated, the Ostwald maturation of the colloidal particles of scarcely soluble active substance is strongly reduced. A new form of pharmaceutical administration having new properties can thus be obtained with generally scarcely water-soluble inorganic and organic compounds, in particular medicaments with a problematic bioavailablity. Preferred medicaments are glibenclamide and 3-indolylacetic acid derivatives, such as indomethacin or acemetacin.

31 Claims, 2 Drawing Sheets

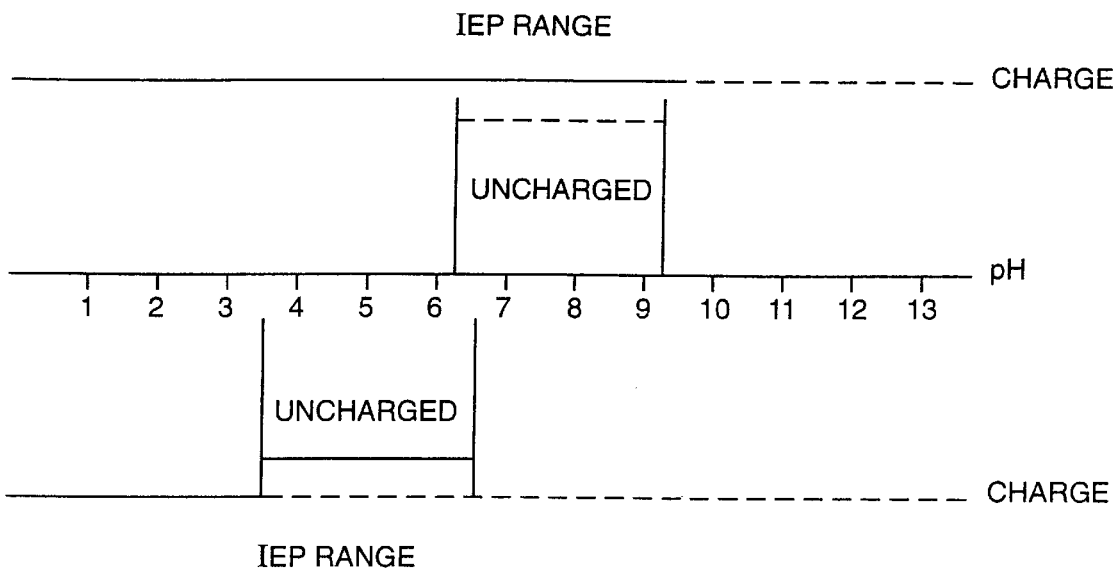
FIG._1

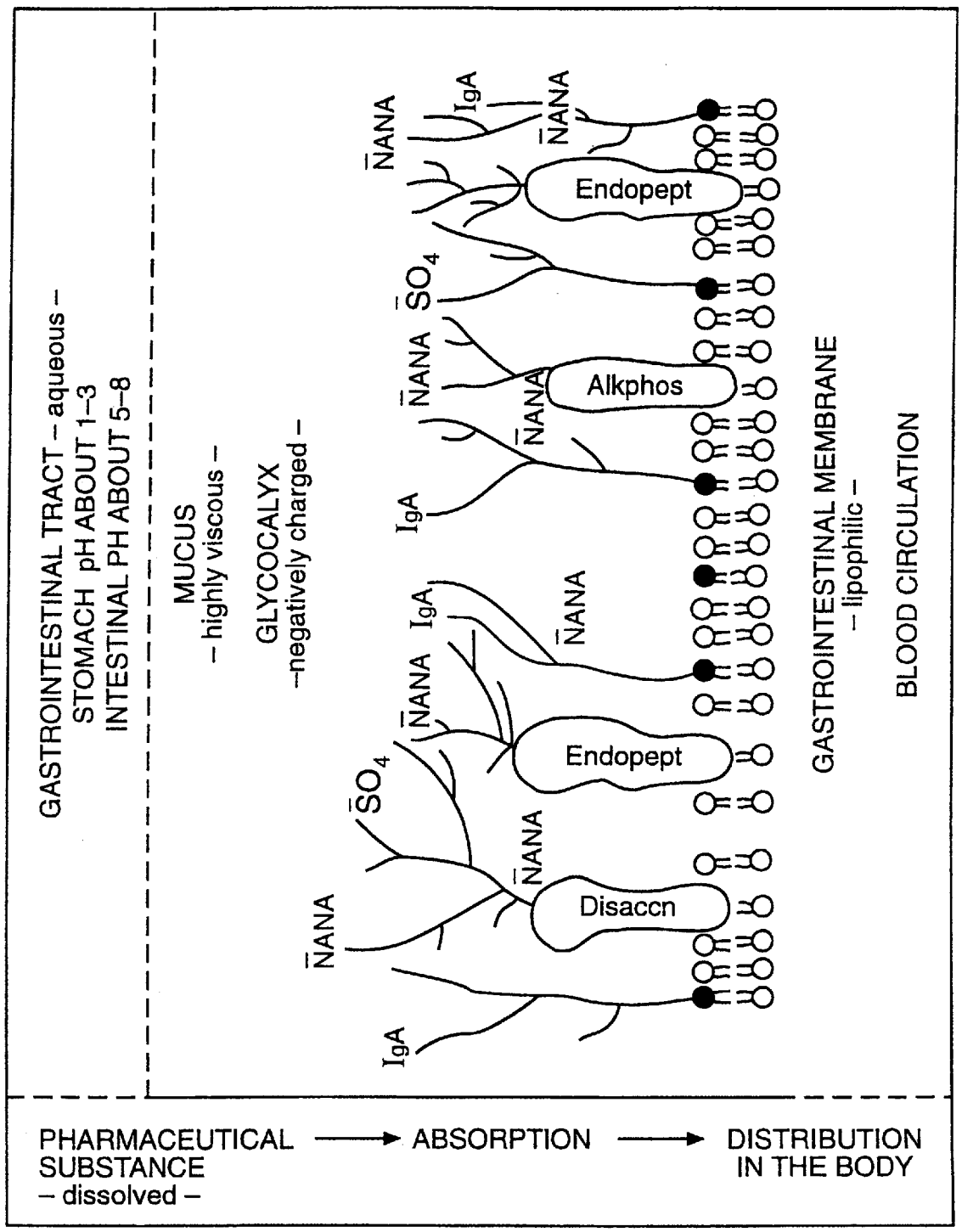
FIG._2

GELATIN OR COLLAGEN HYDROLYSATE CONTAINING DRUG FORMULATION THAT PROVIDES FOR IMMEDIATE RELEASE OF NANOPARTICLE DRUG COMPOUNDS

The present invention relates to a process for the preparation of a colloidally disperse system of poorly water-soluble pharmaceutical substances or of poorly water-soluble inorganic and/or organic compounds. It furthermore relates to a pharmaceutically administrable nanosol, i.e. a stable colloidally disperse system of poorly water-soluble pharmaceutical substances with gelatin. It furthermore relates to an immediate-effect medicament for the treatment of rheumatic and/or inflammatory diseases, which contains a 3-indolylacetic acid derivative. It finally relates to an immediate-effect medicament for the treatment of diabetes, which contains glibenclamide.

The difficulty of bringing pharmaceutical substances with problematic bioavailability into a satisfactory pharmaceutically administrable form is generally known. About 30% of all active compounds in medicaments are included under this group. A rapid release of the active compound from its preparation after administration, i.e. in general a rapid conversion into the dissolved, absorbable form must be demanded of them in order to achieve an acceptable therapeutic result. If it is assumed that the absorption process in vivo is not the rate-determining step, all technological processes for improving pharmaceutical substance release can be attributed to the influencing of two parameters in the so-called Noyes-Whitney equation:

$$\frac{dc}{dt} = \frac{D \cdot A}{d \cdot V}(c_s - c_t),$$

where dc/dt: amount of solid going into solution per time=rate of solution,

D: diffusion coefficient of the substance molecule concerned

A: effective solid or crystal surface which is accessible to the solvent (wettable surface area), d: thickness of the diffusion layer V: solvent volume, $c_s$: saturation solubility of the substance concerned and $c_t$: concentration of the substance concerned in solution at time t.

This equation gives a mathematical expression for the rate of solution of substances generally (in this case pharmaceutical substances). In this equation the changeable target quantities for the pharmacist are only the saturation concentration (saturation solubility) of the pharmaceutical substance and the substance surface area which can effectively be attacked by the solvent. An increase in these two parameters should also result in an increase in the rate of solution.

Classical processes for increasing the saturation solubility of pharmaceutical substances are e.g.:

a) the addition of water-miscible organic solvents, or b) the use of hydrotropic substances.

These measures, however, have the disadvantage that on the one hand they burden the body with toxicologically suspect substances, on the other hand an increased solubility in vivo can be destroyed by the recrystallization processes. Often the amount to be used is additionally inadequate to bring the necessary dose of pharmaceutical substance into solution.

The solubilization of pharmaceutical substances by surface-active, micelle-forming substances or the formation of cyclodextrin inclusion compounds has therefore recently been described. Both applications, however, have the significant disadvantage that primarily dissolved pharmaceutical substance is actually not present in the body in free form, but must be released from its complex with the auxiliary. That is to say on the whole the release of pharmaceutical substance is worsened rather than improved. Apart from this, side effects due to surface-active substances are not to be excluded.

An increase in the surface area of pharmaceutical substances is possible by means of micronization. This processing, however, is very difficult and laborious and has its limit at a particle size of $\geq 1$ μm. The smaller the particles of powder, however, the more strongly prone they are to aerophilicity and the degree of wetting in contact with solvents (effective surface area A) becomes low—the rate of solution is rather reduced. The addition of hydrophilic excipients is therefore almost always necessary.

Further known processes for the preparation of small particles are e.g. the following:

Violanto (U.S. Pat. No. A-4,826,689) describes a method for the preparation of colloidally disperse particles of water-insoluble organic compounds. In this method, laborious test experiments are necessary to determine optimum values for the parameters temperature, rate of stirring and rate of addition of the aqueous precipitation liquid to the solution of the solid compound in the organic solvent. Only keeping to these preconditions ensures the formation of the particles described. A subsequent separation operation is intended to free the particles from the organic liquid. Stabilization measures in certain circumstances require a very time-consuming and expensive zeta potential measurement, according to which an addition of viscosity-increasing substances or surfactants to the aqueous precipitation liquid is calculated which is intended to prevent particle aggregation.

Fessi (EP-A-0 275 796) describes the preparation of a likewise finely dispersed system containing pharmaceutical substances, which, however, requires a defined polymer as the carrier substance. Polymer and pharmaceutical substance are dissolved in a solvent and precipitated using a non-solvent. Steps must subsequently be carried out to remove the nanoparticles, e.g. by filtration or centrifugation. An addition of stabilizer (surfactants or similar excipients) is additionally necessary during preparation in order to minimize particle aggregation.

In the above process, complex additives are always necessary whose use neither can be specifically predetermined nor is desirable from the reasons mentioned at the beginning (toxicological risks). Simple preparation of stable nanosols with as few foreign additives as possible is therefore crucial for pharmaceutically relevant applications.

J. J. Marty et al., Pharm. Acta Helv. 53, 1 (1978) pp. 17–23 describes the preparation of gelatin nanoparticles in which active compounds can also be included. A pH adjustment during the preparation of these gelatin nanoparticles is proposed for desolvation and resolvation. Conversion of the medicament to nanoparticles is not disclosed.

The present invention is therefore based on the object of improving the bioavailability of poorly watersoluble pharmaceutical substances by increasing their rate of solution without addition of harmful auxiliaries.

The invention thus also relates to a nanosol for use in the preparation of a pharmaceutical preparation having improved bioavailability, which contains this nanosol as active component, and the immediate-effect medicament concerned.

The invention furthermore relates to pharmaceutical preparations for use in the treatment of diseases e.g. cardiovascular disorders, rheumatism or gout, diabetes, etc. if they contain a pharmaceutical substance, e.g. nifedipine, indometacin, glibenclamide etc. in the form of nanoparticles in a stable colloidally disperse system with gelatin.

80% of all diabetics suffer from type II diabetes, caused by decreased preparation of insulin. Sulfonylureas, such as e.g. tolbutamide, have proven particularly effective for the treatment of this type. Continuing research activity led to the so-called oral antidiabetics of the 2nd generation, such as e.g. glibenclamide, which excels tolbutamide 300 times in its hypoglycemic action in humans.

Glibenclamide, 1-{4-[2-(5-chloro-2-methoxybenzamido) ethyl]phenylsulfonyl}-3-cyclohexylurea, $C_{23}H_{28}ClN_3O_5S$, of the formula:

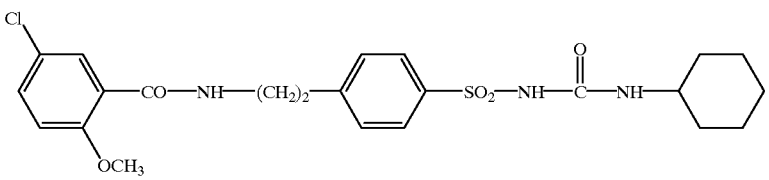

has been largely successful in the market. As comparative in vivo studies verify, no significant differences can be found with respect to the bioavailability quantity serum level surface area (AUC=area under curve). Serious differences exist, however, in the pharmacokinetic parameters $c_{max}$ (maximum blood level value) and $t_{max}$ (the time at which the maximum blood level value is achieved). With many preparations, a delayed onset of action and a lower maximum blood level concentration can be found in comparison to a reference preparation. In particular, however, rapid influx of the glibenclamide is desired. The immediate hypoglycemic effect of glibenclamide is more effective, the more rapidly the active compound is systemically available compared with the carbohydrates. This results in an effective reduction and shortening of the food-related rise in the blood glucose values.

A delayed action with an immediate-effect formulation for glibenclamide can have two causes:

(1) The preparation does not disintegrate rapidly enough, so the release of the active compound is delayed.

(2) The absorption of the active compound is delayed following release.

Comparative in vitro release tests show distinct differences with respect to the tablet disintegration times. The release of some tablets from various manufacturers is delayed, for example only between 50% and 75% of the active compound is released after 30 minutes at pH 7.4. Such a slow release involves various dangers, because this can lead to metabolic derangements in patients, particularly as, especially in the early morning, the blood glucose value, as is known, is at its highest.

The second reason for the deficient biopharmaceutical quality of a glibenclamide preparation has its roots in the fact that the active compound is not absorbed or is only absorbed to a decreased extent in the gastrointestinal tract, especially during passage through the stomach, on account of its pH-dependent poor solubility. According to the passive transport theory, only active compound molecules can be absorbed which are present in dissolved and undissociated form. The solubility of glibenclamide is thus 1 mg/l at a pH of 1.3, 3 mg/l at pH 6.0 and about 30 mg/l at pH 7.8 (the data apply for room temperature in aqueous medium). As an investigation of various absorption sites in the gastrointestinal tract shows, on administration of a dissolved glibenclamide tablet absorption takes place most rapidly in the duodenum.

According to common pharmaceutical knowledge, the solubility of active compounds can be increased even by the use of surfactants which, however, has the crucial disadvantage that primarily dissolved active compound is actually not present in the body in free form, but has to be released from its complex (micelle etc.). This in turn results in a delayed supply of the active compound. The risk of the formation of coarse crystalline components by recrystallization additionally increases. And moreover the use of surfactants is controversial on account of the known side effects and possible toxicity.

As already mentioned above, the water solubility of glibenclamide is pH-dependent. This means that the transition of the active compound into the absorbable form (dissolved and undissociated) depends on the surrounding pH medium of the gastrointestinal tract (GIT). This aspect is worthy of mention in two kinds of respects. Physiological pHs, e.g. those of the gastric fluid, can firstly differ from patient to patient. But the pH of the gastric fluid can also change from case to case, for example due to food absorption (light breakfast, heavy dinner). Such inter- and intraindividual pH changes lead to a differing supply of absorbable components and thus to different blood levels. Thus the onset of action, characterized by release of insulin, is associated with a decrease in blood glucose, which cannot be calculated in terms of time (and according to amount), which can lead to hypo- and hyperglycemic metabolic states. It is common to all commercially available glibenclamide preparations that they are dependent on such individual differences as a result of the pH-dependent poor solubility of the active compound.

The invention furthermore relates to one such medicament which contains 3-indolylacetic acid derivatives, particularly indometacin or acemetacin as the immediate-effect form. The invention finally relates to the use of a pharmaceutically administrable nanosol of 3-indolylacetic acid derivatives, particularly indometacin or acemetacin, for the preparation of medicaments having immediate analgesic and/or antirheumatic effect.

In spite of varied pharmaceutical developments of oral immediate-effect preparations which have a rapid influx, to this day there has still been no success with commercially available medicaments which contain 3-indolylacetic acid derivatives, particularly indometacin or acemetacin, in matching the pharmaceutical form-dependent parameters of active compound release with subsequent absorption of active compound so optimally to the physiological conditions (pH ratios in the gastrointestinal tract, gastrointestinal residence time of shaped articles, specific absorption windows for certain active substances) that the main requirement for an immediate-effect pharmaceutical form is fulfilled:

Reduced time up to the occurrence of the plasma level maximum value ($t_{max}$), e.g. 1 h and less and as a prerequisite for this absorption of the active compound which is as rapid as possible after release from the pharmaceutical form.

This requirement should bring about a high therapeutic efficiency and thus decisively increase patient compliance.

Indometacin, (1-(4-chlorobenzoyl)-5-methoxy-2-methyl-3-indolyl)acetic acid, $C_{19}H_{16}ClNO_4$, which in the meantime is almost already to be designated as the classical, non-steroidal anti-inflammatory, is an active anti-inflammatory substance which plays an important part, particularly in the therapy of immediate-effect attacks of rheumatism and gout. Other syndromes in which treatment with indometacin is indicated are e.g. rheumatoid arthritis, ankylosing spondylitis or osteoarthritis. Indometacin preparations having contents of active compound of 25 mg and 50 mg are commercially available for this purpose.

Acemetacin, carboxymethyl(1-(4-chlorobenzoyl)-5-methoxy-2-methyl-3-indolyl)acetate, $C_{21}H_{18}ClNO_6$, is an ester of indometacin which is for the most part metabolized to indometacin in the metabolism. Its profile of action largely corresponds to that of indometacin. A significant difference should exist, however, in the better tolerability, as acemetacin should only have weakly pronounced ulcerogenic properties in contrast to indometacin.

The problem which has to be overcome in the development of immediate-effect preparations containing said active compounds and which have a rapid influx appears to be as follows, as is made clear by the example of indometacin:

Indometacin is a virtually water-insoluble active compound acid having a $pK_A$ of 4.5. As in general only substances which are present in the body in dissolved and undissociated form are absorbed, no significant absorption of indometacin in the acidic stomach medium (pH 1) is to be expected. Only in the course of further gastrointestinal passage (pH increase in the duodenum) does adequate active compound dissolve such that absorption commences. Correspondingly maximum plasma levels only occur with commercially available indometacin immediate-effect pharmaceutical forms after about 1–3 h ($t_{max}$). These values are to be considered with reservation, because as a result of strong inter- and intraindividual variations in the gastric residence time of oral, non-delayed preparations (e.g. because of the type and amount of food absorbed), a dose of indometacin active compound does not always reach the above absorption range (so-called absorption window) at the predeterminable time. Indometacin is thus one such active compound in which the absorption kinetics always have to be put in relation to the gastrointestinal residence time of the preparation.

Pellets or granules filled in hard gelatin capsules are therefore mainly on the market as preparations, because these can still pass through the stomach relatively rapidly on account of their small diameter (in general 1–1.5 mm). Depending on the type and amount of the food absorbed, the filling state of the stomach etc., average residence times are about 100 min, but can also increase to e.g. up to 300 min.

Knowing these facts, it is easily understandable that a patient suffering from pain takes a second or third dose even before the onset of action of the first dose. The danger of an overdose of course thus increases.

Gelatin is a scleroprotein obtained from collagen-containing material, which has different properties depending on the preparation process. It consists essentially of four molecular weight fractions which affect the physicochemical properties as a function of molecular weight and percentage weight content. The higher e.g. the content of microgel ($10^7$ to $10^8$ D), the higher also the viscosity of the aqueous solution. Commercially available types contain up to 15% by weight. The fraction of α-gelatin and its oligomers ($9.5 \times 10^4/10^5$ to $10^6$ D) is crucial for the gel solidity and is customarily between 10 and 40 percent by weight. Molecular weights below that of α-gelatin are designated as peptides and can amount to up to 80 percent by weight in conventional grades of gelatin (low-bloom).

Depending on the working up of the raw material (acidic or basic hydrolysis), gelatins are obtained whose isoelectric points are different. For acidically hydrolyzed gelatins the IEP is between 6.3 and 9.5 (gelatin Type A), for basically hydrolyzed gelatins it is between 3.5 and 6.5 (gelatin Type B). Other IEPs can also be achieved by means of the special preparation processes indicated below. Common to all types of gelatin, however, is their amphoteric behavior in aqueous medium. At pHs which are not identical to the IEP the macromolecule is always present in charged form.

Depending on the gelatin preparation procedure (extent of breakdown of native collagen and acidic or alkaline hydrolysis process), gelatin of Type A or Type B has a characteristic molecular weight spectrum or molecular weight distribution. Table 1 indicates the molecular weight distributions of various types of gelatin or of collagen hydrolyzates, and the percentage content (frequency) of individual molecular weight ranges.

TABLE 1

Molecular weight distribution of various known types of gelatin or of known collagen hydrolyzates

| Molecular Mass Distribution (kD) | Native Collagen % | Gelatin Type B % | Gelatin Type A % | Collagan hydrolyzate Gelita ® Collagel A | Collagen hydrolyzate Gelita ® Collagel D | Collagen hydrolyzate Gelita ® Sol C | Elastin hydrolyzate Gelita ® Gelastin |
|---|---|---|---|---|---|---|---|
| >360 | 100 | 18.0 | 18.0 | 0 | 0 | 0 | 0 |
| 285 | 0 | 7.0 | 9.0 | 0 | 0 | 0 | 0 |
| 145–237 | 0 | 20.0 | 34.0 | 1.0 | 1.5 | 0 | 0 |
| 95 | 0 | 26.0 | 11.0 | 0 | 0 | 0 | 0 |
| 95–50 | 0 | 16.3 | 13.4 | 2.6 | 4.0 | 1.1 | 0 |
| 50–20 | 0 | 7.4 | 9.1 | 18.0 | 14.5 | 0.3 | 0 |
| 20–10 | 0 | 3.9 | 3.8 | 43.0 | 31.5 | 3.7 | 0.2 |
| 10–5 | 0 | 3.0 | 3.0 | 15.4 | 20.0 | 12.2 | 5.2 |
| 5–2 | 0 | 0 | 0 | 6.0 | 14.0 | 26.0 | 93.9 |
| 2–1 | 0 | 0 | 0 | 7.0 | 8.0 | 23.0 | 0 |
| <1 | 0 | 0 | 0 | 6.5 | 7.0 | 34.0 | 0 |
| MW | 360 | 165 | 185 | 12–18 | 12–18 | 3 | 2–3 |

The predominance of an individual range compared with the other molecular weight ranges of the same gelatin can be seen clearly in the individual columns. This range is thus the maximum of the molecular weight distribution (it is 95 kD e.g. for the Type B gelatin shown in the figure). The concept of the "maximum of the molecular weight distribution", however, is to be separated strictly from the concept of the "average mean molecular weight". This mean value is 165 kD for the gelatin of the Type B mentioned.

Colloidal dispersions are in general metastable and therefore flocculate or sediment. As a result of the predominance of the destabilizing forces, caused by van der Waals attraction, the electrostatic repulsion of the uniformly surface-charged particles is too low so that larger particles grow at the expense of the smaller ones, which is described as Ostwald ripening.

Surprisingly, it is seen in the achievement of the above-mentioned object that with gelatin the adjustment of its state of charge by protonation or deprotonation relative to the isoelectric point (IEP) is completely adequate in order, according to the invention, to stabilize a poorly water-soluble organic compound, in particular such a pharmaceutical substance in the form of a nanosol.

In the context of the invention, it has now been shown that the charged, colloidal pharmaceutical substance particles are stabilized if a charge equalization is achieved between these particles and an oppositely-charged gelatin, a collagen hydrolyzate or a gelatin derivative. This state is the isoionic point (IIP). At the same time, it is surprisingly seen that the Ostwald ripening of the colloidal pharmaceutical substance particles according to the invention is suppressed. The particles are present almost in monodisperse form and are prevented from growth. The entire system is then described as a nanosol according to the invention.

FIG. 1 shows a schematic representation of the adjustable states of charge of gelatins as a function of the pH and IEP, it being possible for the IEP to be between 3.5 and 9.5, depending on the manner of preparation. Below pH 3.5, nearly all types of gelatin are positively charged. In the basic range above pH 9.5, all types of gelatin are negatively charged.

According to the invention the fact is therefore utilized that gelatins, collagen hydrolyzates or gelatin derivatives (nearly independently of the viscosity) lead to a stable colloidally disperse system in nanosol form when the isoionic state of charge is present between pharmaceutical substance particles and gelatin, collagen hydrolyzate or gelatin derivative.

On the other hand, gelatins according to the prior art were only employed for the stabilization of an inorganic, colloidally disperse system. Thus German Pharmacopoeia 9 describes a colloidal injection solution of radioactive gold which is prepared with gelatin. It was merely proposed here that the macromolecule be present as a "cementing substance" between the individual colloid particles and thus particle aggregation be prevented. However, nothing was known until now about the stabilization mechanism, e.g. for pharmaceutical substances.

Other international (PCT) patent applications of ALFATEC Pharma GmbH, where appropriate also the PAZ Arzneimittelentwicklungsgesellschaft mbH, of the same date relate to the immediate-effect form of 2-arylpropionic acid derivatives (81AL2731 corresponding to German Patent Application P 41 40 185.9), the sustained-release form of dihydropyridine derivatives (81AL2732 corresponding to German Patent Application P 41 40 194.8), the immediate-effect form of S- and R-ibuprofen (81AL2733 corresponding to German Patent Application P 41 40 179.4), the sustained-release form of S- and R-ibuprofen (81AL2734 corresponding to German Patent Application P 41 40 172.7), the immediate-effect form of S- and R-flurbiprofen (81AL2735 corresponding to German Patent Application P 41 40 184.0), the sustained-release form of S- and R-flurbiprofen (81AL2736 corresponding to German Patent Application P 41 40 183.2) and the sustained-release form of indolylacetic acid derivatives (81AL2737 corresponding to German Patent Application P 41 40 191.3). Their disclosure is also made the subject of the disclosure of the present patent application.

The degree of loading of the nanosols according to the invention with pharmaceutical substance, expressed in g of pharmaceutical substance per g of gelatin, collagen hydrolyzate or gelatin derivative, in general depends on the dose of the pharmaceutical substance concerned. It can be 1:200 to 1:0.5, and is customarily 1:50 to 1:1, in particular 1:20 to 1:3. The nanosol is thus surprisingly directly very highly suitable for those pharmaceutical substances which usually have to be given in a high dose, such as e.g. ibuprofen (individual dose for analgesic therapy=200 mg, for rheumatic therapy=400 mg). An improvement in bioavailability according to the invention in this case means a dose reduction whose range can be crucial for a therapy. Using less pharmaceutical substance, a more efficient therapy with lower toxic burden on the body is thus possible.

The pharmaceutical substance particles in the nanosol according to the invention preferably have an average particle size of 10 to 800 nm, in particular below 400 nm.

The pharmaceutical substance for the nanosols according to the invention preferably has a solubility in water at room temperature of less than 5 g/l, in particular less than 1 g/l.

If necessary, customary pharmaceutical auxiliaries and/or other macromolecules can be added taking into consideration the stability of the product according to the invention in the liquid or dried state.

Addition of e.g. polyvinylpyrrolidone has proven particularly suitable in technological terms. In this case, in particular with low molecular weight PVP (e.g. PVP K 15), the stability of the nanosol is not decreased. The quantitative ratio of gelatin to polyvinylpyrrolidone in this case can be, for example, in the range from 5:1 to 500:1.

Nanosols may be suitable for the customary types of administration. For example, when using cold watersoluble/modified gelatin the nanosols according to the invention are suitable for use as parenteral preparations. Modified gelatin can be e.g. a commercially available plasma expander. In addition, the nanosols can be used for pulmonary administration or for transdermal application (e.g. semi-solid pharmaceutical form). In particular, however, they are suitable for sublingual and for oral administration and for pharmaceutical forms having bioadhesive properties.

A further advantage of the present invention results from the large width of variation in the types of gelatin which can be used, which advantageously leads to simplified technological applications. By the use of rapidly dissolving types of gelatin, it is thus possible to achieve immediate-effect forms of the nanosol based on tablets which consist almost exclusively of an auxiliary (e.g. direct tableting). Moreover, a nanosol prepared according to the invention can be spray- or freeze-dried without problems even when using high molecular weight grades of gelatin.

Spray-dried nanosols yield an easily dosable or granulatable powder which can be processed to give oral pharmaceutical forms such as e.g. hard gelatin capsules, granules/pellets or tablets.

If the nanosols according to the invention (with or without customary structuring agents) are lyophilized, particularly rapidly releasing pharmaceutical forms can be produced, gelatins having a high peptide content being preferred.

For the preparation of oral sustained-release pharmaceutical forms, sustained-release nanosols can be advantageously prepared, as are described, for example, in the International (PCT) Patent Application having the title "Sol-gesteuerte Thermokolloidmatrix auf Gelatinebasis für perorate Retardarzneiformen" (Sol-controlled thermocolloid matrix based on gelatin for oral sustained-release pharmaceutical forms) from the same applicant on the same date, corresponding to German Patent Application P 41 40 192.1, whose disclosure is also made a subject of the disclosure of the present patent application.

Details of specific pharmaceutical forms which contain poorly soluble active compounds in immediate-effect and/or sustained-release nanosol form can be taken from the applications already mentioned.

In the formulation of immediate-effect or sustained-release preparations, the pharmacist makes a fundamental difference between:

1. pharmaceutical preparation, i.e. of a release of the pharmaceutical substance, e.g. from a tablet in a manner which is rapid (immediate-effect form) or prolonged (sustained-release form) timewise; and
2. the pharmaceutical substance-specific absorption site, such as e.g. the stomach or specific sections of the intestine.

The nanosols according to the invention are able, independently of the pharmaceutical preparation, to be absorbed in the entire gastrointestinal region on account of their special composition. They can therefore be advantageously processed to give immediate-effect or sustained-release pharmaceutical forms.

FIG. 2 shows the mechanism of passive pharmaceutical substance absorption in the gastrointestinal tract.

Suitable pharmaceutical substances for the nanosols according to the invention are furthermore those with problematic bioavailability, in particular:

1. from the strong analgesics groups, e.g. morphine, dextropropoxyphen, pentazocine, pethidine, buprenorphine;
2. from the antirheumatics/anti-inflammatories (NSAR) group, e.g. indometacin, diclofenac, naproxen, ketoprofen;
3. from the β-sympatholytics group, e.g. propranolol, alprenolol, atenolol, bupranolol;
4. from the steroid hormones group, e.g. betamethasone, dexamethasone, methylprednisolone, fludrocortisone and ester, ethinylestradiol, medroxyprogesterone acetate;
5. from the tranquillizer group, e.g. oxazepam, diazepam;
6. from the α-sympatholytics group, e.g. dihydroergotamine;
7. from the hypnotics group, e.g. secbutabarbital, secobarbital, pentobarbital;
8. from the tricyclic antidepressants group, e.g. nortriptyline, clomipramine, amityptiline;
9. from the neuroleptics group, e.g. chlorprothixen, chlorpromazine, haloperidol, trifluopromazine;
10. from the anti-gout agents group, e.g. benzbromarone, allopurinol;
11. from the antiparkinson agents group, e.g. levodopa;
12. from the coronary therapeutics or calcium antagonists group, e.g. nifedipine and other dihydropyridine derivatives, gallopamil;
13. from the antihypertensives group, e.g. clonidine, methyldopa, dihydralazine, diazoxide, renin antagonists;
14. from the diuretics group, e.g. mefruside, hydrochlorothiazide, furosemide, triamterene, spironolactone;
15. from the oral antidiabetics group, e.g. tolbutamide, glibenclamide;
16. peptide pharmaceutical substances, e.g. insulin, renin antagonists;
17. digitalis glycosides;
18. antiarrhythmics;
19. antibiotics/chemotherapeutics, e.g. nitrofurantoin;
20. antiepileptics;
21. anticoagulants;
22. spasmolytics;
23. antimycotics;
24. hormones;
25. venotherapeutics;
26. immunosuppressants, e.g. cyclosporin;
27. tuberculostatics;
28. virustatics;
29. cytostatics;
30. provitamins and vitamins;
31. phytopharmaceuticals;
32. from the group of pharmaceutical substances for the treatment of acquired immune deficiency (AIDS).

Within the meaning of the abovementioned pharmaceutical substance list, enantiomerically pure active compounds or pseudoracemates are also suitable according to the invention.

Furthermore, the nanosols—according to the invention can be used for active substances from the dietetic foodstuffs sector.

It has surprisingly been shown in the context of the present invention that a large number of pharmaceutical substances can be converted into nanosol form if, after selection of a suitable gelatin (Type A or B with characteristic isoelectric point, molecular weight, etc.) such a net charge of the molecule is set which leads to charge neutrality (isoionic point=IIP) with the charged pharmaceutical substance particles and a suitable preparation according to the invention is selected for the pharmaceutical substance (acid, base or neutral substance or amphoteric substance respectively).

Looked at pharmaceutically, the product obtained according to the invention behaves like a true solution, but without having the problems of the prior art; i.e. pharmacologically suspect auxiliaries can be dispensed with.

It is surprisingly seen that the presence of stable nanoparticles e.g. in the case of glibenclamide or of the poorly water-soluble 3-indolylacetic acid derivatives, particularly indometacin or acemetacin, is completely adequate to achieve an absorption of pharmaceutical substance which a) takes place in the stomach immediately on the release of active compound from its preparation;
b) is independent of the physiological conditions described above;
c) is independent of the physicochemical properties of the active compound acid;
d) is nearly complete and
e) takes place without an advance active compound dissolution equilibrium as in the conventional preparations (the active compound is available in absorbable form immediately at any desired site of absorption).

A bioavailability and influx which was previously unknown can thus be achieved with the most different types of active compound. Associated with this is also a reduction in the time from administration up to achievement of the plasma active compound concentration in the therapeutic level. Additionally, the dose of active compound contained in the pharmaceutical form according to the invention is completely utilized such that, looked at all in all, a dose reduction is achieved with it compared with conventional preparations with comparable action. Surprisingly, it has in fact been shown that these nanoparticles in the nanosol according to the invention can pass through the gastrointestinal membrane (be absorbed) unprevented at any desired site of absorption. They thus behave, looked at biopharmaceutically, as a true solution, but without being one.

It has surprisingly been shown that only nanoparticles whose size is in the range from 10–800 nm, preferably below 400 nm, can be absorbed directly. These conditions are fulfilled by the glibenclamide nanosols according to the invention and with 3-indolylacetic acid derivatives, particularly indometacin or acemetacin as active compound.

The advantages of this novel product are thus obvious. As a result of controlled absorption of the active compounds even in the stomach, the rate of influx and bioavailability of glibenclamide and 3-indolylacetic acid derivatives, particularly indometacin or acemetacin, which was previously to be classified as problematical on account of their poor solubility, can surprisingly be significantly improved with a simultaneous increase in the tolerability.

The nanosols employed according to the invention are distinguished by high stabilities, in particular in the acidic range, without flocculating or crystallizing out. This means that the nanosol is available to the gastric mucosa for absorption for a sufficiently long period during the gastric residence period and independent of pH variations which occur, e.g. due to the effect of food.

At pHs below 2, the stability of the nanosol can be further improved by selection of a type of gelatin suited to this pH range.

The particles of the nanosols, after their preparation, after resuspension of the dried powder and after resuspension from a pharmaceutical form, are present in particle sizes from 10 to 800 nm, preferably below 400 nm, and moreover in nearly monodisperse form. In the resuspended state, the nanosol is furthermore well dispersed in the stomach as a nanodispersion, which creates optimum conditions for absorption. As the nano-particles are present in stabilized form, they can be absorbed as such without them previously having to be dissolved. A solution equilibrium in advance as with micronized powders or water-soluble salts is thus unnecessary in any case. They therefore behave, looked at biopharmaceutically, as a true solution, but without being one of these.

For the first time, controlled absorption in the gastrointestinal tract is possible even during the gastric residence time as a result of the present invention. The absorption is no longer restricted to the small intestine region; a rapid influx of glibenclamide and of 3-indolylacetic acid derivatives, particularly indometacin or acemetacin, is facilitated.

It is thus surprisingly possible to achieve a $t_{max}$ value of less than 1 h, in particular less than 30 min, with these pharmaceutical substances for the first time.

Additionally, an increase in the blood level maximum value $c_{max}$ can also be determined. The increase in $c_{max}$ can therefore in certain circumstances result in a dose reduction with the same activity.

As in vitro experiments have shown, the danger of recrystallization in the stomach can be excluded as a result of the mentioned long stabilities of the nanosols according to the invention.

Furthermore, the immediate-effect form of glibenclamide or of 3-indolylacetic acid derivatives can also be combined with a sustained-release formulation of glibenclamide or 3-indolylacetic acid derivatives.

As a particular embodiment, a powdered or granulated immediate-effect nanosol can be combined with a matrix tablet, as is described in the abovementioned International (PCT) Patent Application having the title "Sol-gesteuerte Thermokolloidmatrix auf Gelatinebasis für perorate Retardformen" (Sol-controlled thermocolloid matrix based on gelatin for oral sustained-release forms) of ALFATEC-Pharma GmbH of the same date, e.g. in a hard gelatin capsule. The contents of said application are also made the contents of the present patent application.

Such a pharmaceutical form initially releases the active compound rapidly and the maintenance dose (matrix tablet) constantly with high reproducibility according to a zero order rate law.

The dried nanosol can be processed to give pharmaceutical forms, for example to give a tablet, and resuspended from this. An enteric coating for protection from "inactivation" of the active compounds by the acidic stomach pH is thus superfluous.

The danger of an overdose due to taking repeatedly is excluded by the rapid onset of the therapeutic effect as a result of absorption in the stomach. All the disadvantages and dangers of an enteric coating are inapplicable. The present invention thus also serves to increase patient compliance. This all constitutes a decisive contribution to the medicament safety demanded.

Fundamentally, the product according to the invention can be processed to give all pharmaceutical forms which are to be administered orally, in particular it can be filled into hard gelatin capsules directly as a powder. It is also outstandingly suitable for direct tableting. Processing to give beverage granules, rapidly dissolving pellets or beverage tablets is of particular interest for administration as an immediate-effect form which has a rapid influx.

In order to explain the physiological background of the absorption of pharmaceutical substances in general and the improved absorption ratio of the nanosols according to the invention adequately, first a consideration of the mechanism of physiological absorption of pharmaceutical substances as is also presented in relevant publications is necessary. However, the present invention is neither tied to the following attempt of a scientific explanation of the phenomena occurring according to the invention nor can it be restricted by this.

Passive pharmaceutical substance absorption takes place according to the modern state of knowledge (theory according to Brodie et al.), if the following conditions exist:

a) the gastrointestinal membrane acts as a lipid barrier, b) the pharmaceutical substance is only absorbed in dissolved and uncharged, i.e. nonionized form, c) acidic pharmaceutical substances are preferably absorbed in the stomach and basic pharmaceutical substances preferably in the intestine.

After the oral uptake of a pharmaceutical substance into the body, its absorption, i.e. the crossing into the general circulation (biophase) is prevented to a great degree by physical barriers (see FIG. 2), namely by the mucus layer and an aqueous layer adhering thereto the cell membranes of the intestinal epithelial cells with the glycocalyx bonded thereto and the so-called "tight junctions" which connect the epithelial cells with one another on their apical sides.

These barriers presuppose that absorption of pharmaceutical substances takes place through the lipid double layers fundamentally independently of their distribution mechanism and state of charge (so-called passive diffusion).

The epithelial cells of the entire gastrointestinal tract are covered with a mucus layer which consists of mucins (glycoproteins), electrolytes, proteins and nucleic acids. In particular, the glycoproteins form with the main components of mucus, namely water, a viscous gel structure which primarily performs protective functions for the underlying epithelial layer. The mucus layer is bound to the apical surface of the epithelial cells via the glycocalyx. The glycocalyx likewise has a glycoprotein structure which is covalently bonded to components of the membrane double layer of the epithelial cells. The branched polysaccharides of the glycocalyx, which are either directly covalently bonded to amphiphilic molecules of the double membrane or to proteins incorporated in the double membrane, possess charged N-acetylneuraminic acid and sulfate radicals and are therefore negatively charged, which can lead to an electrostatic bond or repulsion of charged pharmaceutical substance molecules or of electrostatically charged particles respectively. The epithelial cell membranes consist of phospholipid double layers in which proteins are anchored via their hydrophobic regions. The phospholipid double layers with their lipophilic content represent a further barrier for the transport of the pharmaceutical substances to be absorbed.

From this description, it clearly follows that charged pharmaceutical substance molecules or electrostatically charged particles therefore only have a very low chance of being absorbed via the oral administration route.

The nanosols according to the invention for the first time provide the technical teaching to form a system with which these abovementioned obstacles to absorption can be overcome. As the active compound nanoparticles are stabilized in neutrally charged form by the gelatin according to the invention, they can be transported through the negatively charged glycocalyx without relatively great obstructions, in contrast to other described nanoparticles of the prior art, which are not or cannot be stabilized in neutrally charged form. According to the invention, the adjustment of the isoionic state of charge can additionally be effected in coordination with the physiological conditions.

As the active compound nanosols according to the invention can pass through the glycocalyx without obstacle, without being bonded or repelled by electrostatic effects, they thus also reach the surface of the epithelial cells and are available there in a high concentration.

Active, carrier-mediated transport mechanisms or phagocytosis can now also make a significant contribution to the absorption of the active compound nanosols.

According to the invention, the following advantages compared with the prior art are thus especially achieved:

poorly water-soluble inorganic and organic compounds are brought into a form having novel properties;

the process is applicable to nearly all poorly soluble inorganic and organic compounds;

it can be carried out simply and without complicated equipment and apparatuses;

pharmaceutical substances which are poorly soluble or absorbable in the body can thus be converted into a form which behaves like a true solution;

this takes place without chemical change, e.g. without the formation of a derivative, or formation of a chemical complex;

this takes place without addition of surface-active or hydrotropic substances;

compounds which are difficult to dissolve are more rapidly and completely absorbable in vivo in this form;

the dose can be reduced;

the form obtained is stable on storage;

the biopolymer gelatin or its derivative is a toxicologically acceptable auxiliary;

gelatin in immediate-effect or sustained-release forms contributes to good tolerability of the pharmaceutical substance formulated according to the invention;

the preparation processes indicated are economical.

The system according to the invention is completely independent of individual differences as far as pH variations or pH effects, e.g. due to food, are concerned. An onset of action which cannot be calculated in terms of time (and according to amount), as can be the case with products of the prior art, is thus to be excluded and the risk of side effects is reduced. The present invention thus represents a decisive contribution to the demanded pharmaceutical safety.

Fundamentally, the product according to the invention can be processed to give all pharmaceutical forms to be administered orally, in particular it can be filled into hard gelatin capsules directly as a powder. It is also outstandingly suitable for direct tableting. Processing to give beverage granules, rapidly dissolving pellets or beverage tablets is of particular interest for administration as an immediate-effect form having rapid influx.

In principle, all procedures and process variants and the preparation of gelatin (Examples 1 to 3) mentioned in the present application of ALFATEC-Pharma GmbH are suitable for the preparation of the nanosols used according to the invention. In the case of the immediate-effect form of glibenclamide, variants Nos. II and III may be mentioned as preferably suitable processes for nanosol preparation (see below).

Gelatin is a scleroprotein obtained from collagen-containing material which has differing properties according to the preparation process. Molecular weight ranges from a few thousand D up to a few million D exist, which can be very different in their molecular weight composition and in their physicochemical behavior. With exact knowledge of these relationships, novel pharmaceutical applications can be found which are distinguished by high reproducibility and simple technological processing. Details can be taken from the above-mentioned applications. With a particularly gentle preparation procedure, types of gelatin can be obtained which only have a low content of dextrorotatory amino acids and are thus constructed similarly to the native collagen molecule. These gelatins are distinguished, for example, by particularly good stability properties for nanosols. Such a gelatin is advantageously suitable according to the invention. Depending on the working up of the raw material (acidic or basic decomposition), gelatins are obtained whose isoelectric points are very different. By means of special preparation techniques, isoelectric points can be produced specifically, it being possible to suit the molecular weight distribution to the application.

In the case of glibenclamide, types of gelatin are preferably suitable whose molecular weight distribution maximum is below $10^5$ D. For tablet preparation, as is usually predominant with oral antidiabetics, suitable types of gelatin are preferably those having bloom values of 0–50 and a maximum in the molecular weight distribution in the range $10^4$–$9.533 \cdot 10^4$ D.

With the gelatins mentioned, a weight ratio of gelatin to active compound of 1:1 to 200:1 can be set, a higher weight ratio being advantageously selected during processing to give tablets etc. to avoid further auxiliaries (e.g. direct tableting).

Commercially available gelatins, fractionated gelatins, collagen hydrolyzates and gelatin derivatives, in particular those types which are characterized by a low bloom number of 0 (cold water-soluble gelatins or collagen hydrolyzates) up to 240 bloom, preferably 0 to 170 bloom, are suitable for the nanosols used according to the invention containing glibenclamide or indometacin.

In the case of glibenclamide, types of gelatin with IEPs of 3.5 to 7.5 are preferably employed.

For spray- or freeze-drying of glibenclamide nanosols, addition of polyvinylpyrrolidone (PVP) to the aqueous gelatin solution, in particular PVP K 15 or PVP K 25 in the weight ratio from 1:5 to 1:30 has been shown to be advantageous, a readily pourable powder being obtained without adverse effect on the stability of the nanosol.

In principle, commercially available gelatins, highly degraded gelatins (collagen hydrolyzates or cold water-soluble gelatin), modified gelatins and fractionated gelatin (single fractions or mixtures thereof) are also suitable for the preparation of the nanosols according to the invention.

Too high a content of foreign ions (ash content >2%), however, can have an interfering effect and should be removed by deionizing using ion exchange resins (for gelatin see generally: Ullmann, Encyclopädie der technischen Chemie (Encyclopedia of Industrial Chemistry), 3rd Edition, 1954, Vol. 10 and 4th Edition, 1976, Vol. 12, p. 211; H. E. Wunderlich: Wenn es um Gelatine geht (When to use Gelatin)—publisher: Deutscher Gelatine-Verbraucherdienst, Darmstadt (1972); I. Tomka, Gelatin, in: W. Fahrig, U. Hofer, Die Kapsel (The Capsule), Wissenschaftliche Verlagsgesellschaft mbH Stuttgart, 1983, pp. 33–57.

Compared with commercially available products, the use of gelatin which has been prepared in a special manner leads to nanosols described according to the invention having increased stability.

Examples of the preparation of grades of gelatin particularly suitable according to the invention are given below.

Examples of the preparation of particularly suitable types of gelatin according to the invention with isoelectric points of 3.5 to 9.5

EXAMPLE I

Process for obtaining IEPs of 7.5 to 9.5

Collagen-containing starting material such as e.g. pig skins are treated for 12 to 20 hours with an aqueous solution of a 0.45N mineral acid, preferably sulfuric acid, in a liquor ratio of 1:1. The excess of acid is then removed by washing several times, it being possible to use sodium hydrogen carbonate to shorten the process. The extraction of the stock-rich material is carried out using hot water at 55–80° C. at a pH of 2.5 to 4.5. At pHs below 3.5 an IEP of 8.5 to 9.5 can be achieved, at pHs above 3.5 the IEP is 7 to 8.5. In this manner, various IEPs from 7 to 9.5 can be achieved as a direct function of the pH during the extraction.

After the extraction process step, the aqueous solution is neutralized and worked up as customary.

Depending on the temperature selected during the extraction, types of gelatin having high to medium molecular weight distributions can furthermore be obtained by this process.

At temperatures of 50–55° C., particularly highly viscous and high-bloom grades are obtained. Types of gelatin having low molecular weight or cold water-soluble gelatins can be obtained by controlled degradation with collagenases.

EXAMPLE II

Process for achieving an IEP of 4 to 7.5

The collagen-containing starting material is first washed to remove foreign substances and comminuted, and then homogeneously rendered alkaline by addition of magnesite, sodium hydroxide solution or calcium hydroxide by thorough mixing in the liquor ratio 1:1.2. The material pretreated in this way is briefly hydrolyzed by pressure hydrolysis at $1.01 \times 10^5$ to $2.02 \times 10^5$ Pa and a pH of the aqueous solution of 8–14. After hydrolysis, it is immediately neutralized and the still hot aqueous gelatin solution is filtered, deionized, concentrated and dried in the usual manner.

If a weakly basic hydrolizing agent such as magnesite is taken, an IEP of 6 to 7.5 is obtained if the reaction is carried out at $1.01 \times 10^5$ Pa. IEPs of 5 to 6 are obtained when using a dilute milk of lime suspension and when using 0.005 to 0.1N sodium hydroxide solution IEPs of 4 to 5 can be achieved.

Types of gelatin having a low degree of racemization and a low peptide content can be obtained with pressure ratios of $1.01 \times 10^5$ Pa and residence times of at most 10 min.

Medium to low molecular weight types to cold water-soluble types are produced by correspondingly longer residence times.

EXAMPLE III

Process for achieving an IEP of 3.5 to 6

Collagen-containing starting material, preferably split or ossein is subjected after the starting wash to treatment with a high-speed asher. In this case, two process variants in the liquor ratio 1:1.3 offer themselves, which either use a saturated milk of lime suspension or a 0.1 to 1N sodium hydroxide solution.

When using a milk of lime suspension, the raw material is hydrolyzed for a maximum of 3 to 4 weeks with continuous agitation. The material is then neutralized by addition of acid and washed several times. Further working up follows in the usual manner. IEPs of 4 to 6 can be obtained in this manner.

When using sodium hydroxide solution, the asher process can be shortened again, the material, depending on the degree of comminution, being hydrolyzed even after 6–12 hours at concentrations of 1N sodium hydroxide solution. Neutralization is carried out using equimolar amounts of mineral acid and the neutral salts are removed by washing several times or by deionizing the aqueous gelatin solution obtained in the extraction. In this process variant, IEPs of 3.5 to 5 can be obtained.

Particularly low-peptide types of gelatin are obtained with a short residence time in the asher. Types of gelatin with high to average molecular weight distribution ($M=10^4-10^7$ D) can thus be obtained.

Low molecular weight to cold water-soluble types of gelatin can be obtained by thermal degradation or enzymatically.

As already mentioned at the beginning and as is evident from FIG. 1, the absolute, maximum possible net charge of an individual gelatin molecule depends mainly on the number of free COOH and $NH_2$ groups and the pH of the solution. As Type A, B, collagen hydrolyzates or gelatin derivatives differ in the number of free COOH groups, their maximum possible net charge is thus also different. With gelatin derivatives, the state of charge can additionally depend on the type of modification.

When carrying out the process according to the invention, the suitable gelatin and the suitable pH are selected in a preliminary test.

First, a working pH range suited to the physicochemical properties of the pharmaceutical substance is selected. Physicochemical properties of the pharmaceutical substance to be taken into account in particular are: the solubility (in organic solvents or water), its properties as an acid, base or neutral substance and its stability to acids and alkali solutions.

In a first rapid test it is determined what charge the precipitated particles have. This results, taking into account the working pH range, in the choice of a suitable type of gelatin. If the particles are, for example, negatively charged, a gelatin is picked which is positively charged under the given pH conditions. This rapid test for the determination of the particle charge has the advantages that it can be carried out without a great outlay in terms of apparatus and time. A timeconsuming and inaccurate zeta potential measurement can thus be dispensed with entirely.

In many cases, it will be adequate for this rapid test to convert two commercially available Type A and B gelatins with an IEP of 9.5 or 3.5 respectively and with peptide contents of <30% and a bloom number of 200, which are furthermore designated as standard gelatins, into the sol form at a pH of 6 (5% strength aqueous solution) and to dissolve the pharmaceutical substance in a water-miscible solvent, such as e.g. ethanol, isopropanol or acetone, and in each case to mix homogeneously with the gelatin solutions. At the same dose of the pharmaceutical substance, in the case of the gelatin which is unsuitable in its state of charge a colloidal system will either not form or immediately become unstable or the pharmaceutical substance will flocculate. If the resulting particles are negatively charged, they are stabilized rather by the gelatin solution of Type A, which is positively charged at a pH of 6, than by the solution containing Type B gelatin; in contrast, in this case Type B either will form no colloidal system or the system will immediately destabilize. The flocculation of the particles can be monitored e.g. via a simple turbidity measurement.

In this rapid test, the working pH range must be taken into account in each case. Other gelatins can also be selected as standards, but they must be selected in their IEP such that they carry an opposite net charge at this pH (see also FIG. 1). In most cases, said standard Type A and B gelatins are adequate for this rapid test.

Starting from the result of the preliminary experiment, the optimum conditions for the formation of the nanosols are determined by stepwise variation of the IEPs by use of appropriate types of gelatin and of the pH of the solution in relatively small ranges (e.g. 0.1 pH steps), i.e. the stability optimum which is characterized by the isoionic point (IIP) must be found in order to guarantee an adequate stability for the pharmaceutical applications mentioned.

It can be the case that a stability of the nanosols which is acceptable within the meaning of the invention is already found in a relatively narrow pH range (about 0.5 units) around the isoionic point, so an adjustment of this point itself is not absolutely necessary. On the other hand, several gelatins can also lead to the same, stable results. Thus, for example (Example 5) with the oral antidiabetic glibenclamide in the case of a Type B gelatin with an IEP of 5.5 the stability optimum can be at a pH of 3.2, while in the case of a Type B gelatin with an IEP of 3.8 the stability optimum is at a pH of 2.2.

Characterized by a stability maximum, in both cases the isoionic point was reached (the dependence of the net charge on the pH and the IEP must be non-linear, as it is given by the $pK_a$ value of the COOH or $NH_3^+$ groups present).

According to the invention, other macromolecular substances in addition to gelatin, collagen hydrolyzates, fractionated gelatin or gelatin derivatives can be added in small amounts (at most 5% by weight). These can be amphoteric or charged substances, such as, for example, albumins, casein, glycoproteins or other natural or synthetic polypeptides. In particular cases, anionic polymers such as e.g. alginates, gum arabic, pectins, polyacrylic acids and others may also be suitable.

According to the invention, several processes for the preparation of the nanosols are proposed. These are an exemplary, incomplete list. The person skilled in the art can independently work out further variants in the context of the present invention on the basis of his expert knowledge:

Process I

This can be used if the pharmaceutical substance is soluble in a mixture of: a water-miscible organic solvent and water, or several water-miscible organic solvents and water:

a) a gelatin selected in the preliminary tests is converted into sol form with water;

b) the pH of the solution found in the preliminary tests is adjusted;

c) one or more water-miscible, organic solvent(s), preferably ethanol, isopropanol or methanol, is/are added to this solution;

d) the pharmaceutical substance is added to the solution in solid form and dissolved;

e) the organic solvent(s) is/are removed, preferably by evaporating in vacuo; the nanosol is formed during the course of this;

f) the colloidally disperse solution is then dried, preferably by spray- or freeze-drying.

The organic solvent has the aim of dissolving the pharmaceutical substance and also changes the hydration shell of the gelatin molecules.

Process II

This embodiment can be used if the pharmaceutical substance is an acid or a base whose salt is soluble in water:

a) a gelatin selected in the preliminary tests is converted into the sol form with $H_2O$;

b) a pH is set which enables formation of the salt of the pharmaceutical substance;

c) the pharmaceutical substance is dissolved in the gelatin sol with salt formation;

d) by addition of alcohol or similar organic solvents, the hydration shell of the gelatin molecules can be loosened;

e) by addition of a suitable amount of acid or base the pH is set which leads to the formation of the isoionic point (IIP) and the nanosol results;

f) the colloidally disperse solution is dried as in process I. Stage d) is optional, but preferred.

Process III

This embodiment can be used if the pharmaceutical substance is a neutral substance:

a) a gelatin sol is prepared as described in (1) a) and b).

b) a second solution is prepared from a water-miscible organic solvent, preferably ethanol, methanol, isopropanol or acetone and the pharmaceutical substance.

c) the two solutions are combined.

d) the original solvent is removed and the colloidally disperse solution is dried.

Process IV a) As described in (I) a) and b).

b) A collodially disperse system is briefly formed with the pharmaceutical substance, but without gelatin, in a second solution.

c) The solution obtained in (b) is continuously combined with the gelatin solution.

In step (IV) c) the continuous mixing of the solutions described in (IV) a) and b) can be controlled particle size using a suitable process, such as e.g. by laser light scattering (BI-FOQELS On-line Particle Sizer). It is thus possible to continuously set a desired particle size.

All processes mentioned are also suitable for collagen hydrolyzates and gelatin derivatives and can be applied without problems on the industrial scale.

The essential steps can largely run in an automated manner, it also being possible to carry out processes I to III continuously.

A pharmaceutically administrable nanosol and a process for its preparation with various embodiments is described above. The invention, however, relates very generally to a nanosol, i.e. a stable highly disperse system of poorly water-soluble inorganic and/or organic compounds with gelatin, which comprises a) an inner phase of the inorganic and/or organic compound(s), which has (have) a particle size of 10 to 800 nm and possesses (possess) a negative or positive surface charge, b) an outer phase of gelatin, collagen hydrolyzate or a gelatin derivative, which is positively or negatively charged, c) an approximately or completely isoionic charge state of the inner and outer phase.

Such a nanosol can be present as a liquid, aqueous nanodispersion. However, it can also be present as a solid, resuspensible nanodispersion. A nanosol is particularly preferred in which the inorganic and/or organic compound or organic compounds has (have) a particle size distribution of less than 300 nm, in particular 10 to 100 nm. With positively charged particles of the organic compound(s), the gelatin has a negative net charge, while with negatively charged particles of the organic compound(s) it has a positive net charge.

The process for the preparation of such a nanosol from poorly water-soluble inorganic and/or organic compounds is carried out by the process which was described above in connection with the preparation of pharmaceutically administrable nanosols.

The following examples are intended to illustrate the invention in greater detail:

EXAMPLE 1

Pharmaceutical substance: ibuprofen (racemate), active compound acid
Gelatin type: commercially available, Type B, 170 bloom
Nanosol preparation: analogous to Process I
Weight ratio gelatin/pharmaceutical substance: 1.5:1

The working pH range for ibuprofen is preferably below its $PK_a$ of 4.6.

The preliminary test at pH 4.3 for determination of the surface charge of the ibuprofen particles does not yield a nanosol with the standard gelatin Type B (IEP 3.5/200 bloom). Under identical test conditions the standard gelatin Type A (IEP 9.5/200 bloom) yields a briefly stable nanosol, in which the ibuprofen particles present carry a negative surface charge.

For the determination of the stability optimum, types of gelatin with various IEPs are then tested at various pHs below pH 4.3. The series of measurements shows that a gelatin of Type B (IEP 4.9), which carries a positive net charge at pH 3, is best suited. The nanosol formed according to process I has a stability maximum suitable for pharmaceutical use.

500 g of a 3% strength aqueous gelatin solution of the abovementioned type are brought to pH 3.

250 ml of 96% ethanol are added.

10 g of ibuprofen are dissolved in this mixture, then the organic solvent is evaporated. The nanosol thus produced is then spray-dried and can be processed to give the corresponding pharmaceutical form.

Particle size measurements using a BI-FOQELS On-Line Particle Sizer reveal to 65% particle sizes of 450 nm.

EXAMPLE 2

The procedure is as in Example 1, but a gelatin is used which has been obtained according to Example III (gelatin preparation) having the same bloom value and the same IEP (4.9).

Particle size measurements reveal to 70% particle sizes of 265 nm.

EXAMPLE 3

Pharmaceutical substance: dexamethasone, neutral substance
Gelatin type: Type A, 220 bloom, preparation Example I
Nanosol preparation: analogously to Process III
Weight ratio gelatin/pharmaceutical substance: about 10:1

The preliminary test carried out at pH 7 analogously to Example 1 reveals in the case of the neutral substance dexamethasone that a Type A gelatin is suitable.

A Type A gelatin (IEP 7.9) having a positive state of charge at pH 5.3 yields the stability optimum.

500 g of a 7.5% strength aqueous gelatin solution of the type of gelatin specified above is adjusted to pH 5.3 by addition of acid.

3.5 g of pharmaceutical substance are dissolved in 100 ml of acetone.

Both solutions are mixed and the resulting nanosol is spray-dried after removal of the organic solvent.

The average particle size of the nanosol is between 260 and 300 nm.

EXAMPLE 4

The nanosol is produced as in Example 3, but using a gelatin of commercially available grade with identical characteristic numbers.

The average particle sizes are in the range from 550 to 630 nm.

EXAMPLE 5

Pharmaceutical substance: glibenclamide, active compound acid
Gelatin type: Type B, 100 bloom, preparation

EXAMPLE III

Nanosol preparation: analogously to Process III Weight ratio gelatin/pharmaceutical substance: 100:1

The working pH range for the weak active compound acid glibenclamide is preferably below its $PK_a$ of 6.3 to 6.8.

The preliminary test according to the invention and the series of measurements reveals an optimum with a Type B gelatin (IEP 3.8) at a pH of 2.2 for the isoionic charge state.

For nanosol preparation, 5 g of gelatin of the above type are then converted to 5% into the sol form with water.

50 mg of glibenclamide are dissolved in 30 ml of 96% ethanol and homogeneously mixed with the aqueous gelatin solution.

The resulting nanosol is lyophilized after removing the organic solvent on a rotary evaporator.

Average particle sizes are 130 nm.

EXAMPLE 6

Pharmaceutical substance: propranolol, active compound base
Gelatin type: Type B, 320 bloom, preparation Example II
Nanosol preparation: analogously to Process II
Weight ratio gelatin/pharmaceutical substance: 4:1
Working pH range: 9.2
Gelatin selected according to preliminary test: Type B, 320 bloom, IEP 4.2

16 g of propranolol hydrochloride are dissolved at pH 3 in a warm gelatin solution (64 g and 640 ml of water). By addition of sodium hydroxide solution a pH of 8.8 is set, at which a nanosol of the propranolol base is formed. In this case the isoionic charge state is only approximately achieved.

The average particle sizes vary more greatly and are in the range from 650 to 780 nm.

EXAMPLE 7

Pharmaceutical substance: indometacin, active compound acid
Gelatin type: collagen hydrolyzate having a peptide content of 90%, preparation Example II
Nanosol preparation: analogously to Process II
Weight ratio gelatin/pharmaceutical substance: 5:1

The preliminary test is carried out as in Example 1, but at a pH of 4.0.

The stability optimum of the nanosol is achieved with the collagen hydrolyzate having an IEP of 5.2 and a pH of the aqueous pharmaceutical substance/gelatin solution of 3.1.

150 g of the collagen hydrolyzate are dissolved in 2 l of distilled water. 30 g of indometacin are suspended in this solution. The pH of the system is kept between 7 and 8 using sodium hydroxide solution. It is additionally stirred until a completely clear solution is formed. By addition of a measured amount of hydrochloric acid, the pH is adjusted to 3.1, at which the nanosol spontaneously forms.

The nanosol solution obtained is concentrated and spray-dried. The powder obtained is processed to give an immediate-effect form.

Particle size measurement reveals to 70% particle sizes of less than 370 nm.

EXAMPLE 8

Pharmaceutical substance: nifedipine, neutral substance
Gelatin type: commercially available, Type B, 60 bloom
Nanosol preparation: analogously to Process III
Weight ratio gelatin/pharmaceutical substance: 15:1

Preparation is carried out with protection from light (yellow light).

The preliminary test is carried out analogously to Example 1, but at a pH of 6.0.

The following series of measurements for the determination of the stability optimum shows a Type B gelatin (IEP 4.7) at a pH of 5.5.

600 g of the completely deionized gelatin specified above and 40 g of PVP K 15 are dissolved in 8 l of distilled water at 40° C. and adjusted to a pH of 5.5.

40 g of nifedipine are completely dissolved in 1.3 l of ethanol.

Both solutions are homogeneously mixed and the resulting nanosol is spray-dried after removal of the alcohol. The powder obtained is filled into opaque hard gelatin capsules with a content of 10 mg of nifedipine per capsule.

The dissolution test (paddle) reveals 100% release after 9 minutes (75 rpm/900 ml of 0.1N HCl).

The bioavailability is increased by 25% in vivo compared with a conventional capsule preparation containing micronized nifedipine. Maximum blood level values are achieved on average after 20 min.

EXAMPLE 9

Active compound: glibenclamide, active compound acid
Gelatin type: commercially available, Type B, molecular weight below $10^4$ D
Nanosol preparation: analogously to Process III
Weight ratio gelatin/pharmaceutical substance: 35:1

The working pH range is below the $pK_a$ of 6.3–6.8.

After carrying out the preliminary test according to the invention and the series of measurements for the determination of the optimum type of gelatin, a stability maximum with a Type B gelatin (IEP 3.8) at a pH of 2.2 is determined.

500 g of the above gelatin are dissolved in 3 l of dist. water. A pH of 2.2 is set by addition of hydrochloric acid.

13.89 g of glibenclamide are dissolved in 0.2 l of ethanol. The two solutions are combined, whereupon the nanosol forms.

Particle size measurements reveal to 80% particle sizes of less than 380 nm.

The organic solvent is removed in vacuo and the product is then spray-dried.

The dried nanosol is shaped to give tablets with addition of customary tableting auxiliaries in an eccentric press. Tablets having a rapid influx in each case with a content of 3.5 mg of glibenclamide result.

EXAMPLE 10

Active compound: glibenclamide, active compound acid
Gelatin type: Type B (IEP 3.8), 20 bloom, preparation Example III
Nanosol preparation: analogously to Process III
Weight ratio gelatin/active compound: 35:1

Preparation of the nanosol is carried out analogously to Example 9.

Particle size measurements reveal to 80% particle sizes of less than 180 nm.

EXAMPLE 11

Active compound: indometacin, active compound acid
Gelatin type: commercially available, Type B, 60 bloom
Nanosol preparation: analogously to Process II
Weight ratio gelatin/active compound: 6:1

The working pH range is below the $pK_a$ of 4.5.

After carrying out the preliminary test according to the invention and the series of measurements for the determination of the optimum type of gelatin, a stability maximum with a Type B gelatin (IEP 5.2) at a pH of 3.1 is determined.

600 g of the above gelatin are dissolved in 10 l of dist. water. 100 g of indometacin are suspended in this gelatin solution. Sodium hydroxide solution is added so that the pH of the system is set in the range 7–8. The mixture is additionally stirred until a clear solution is formed. It is then adjusted to pH 3.1 by addition of hydrochloric acid, whereupon the nanosol forms.

The water is removed by subsequent spray-drying. The dried nanosol is processed to give tablets in an eccentric press with the addition of customary tableting auxiliaries. Tablets having a rapid influx in each case with an indometacin content of 50 mg result.

Particle size measurements (BI-FOQUELS on-line Particle-Sizer) reveal average particle sizes of about 370 nm.

EXAMPLE 12

Analogously to Example 11, only the gelatin is mixed with 10 g of polyvinylpyrrolidone K 15 before preparation of the solution.

Particle size measurements reveal average particle sizes of about 390 nm.

In a dissolution test according to USP (750 ml test volume, consisting of 1 part by volume of phosphate buffer pH 7.2 and 4 parts by volume of water, paddle, 100 rpm, 37° C.), a complete dissolution of the tablet results within 15 minutes. In comparison with this, tablets from Example 11 are investigated under identical test conditions and show dissolving times which are 20% higher on average.

EXAMPLE 13

Active compound: indometacin, active compound acid
Gelatin type: collagen hydrolyzate (IEP 5.2), preparation according to Example II
Nanosol preparation: analogously to Process III
Weight ratio gelatin/active compound: 4:1

300 g of the gelatin specified above are dissolved in 3 1 of distilled water and a pH of 3.1 is set.

75 g of indometacin are dissolved in 500 ml of isopropanol. Both solutions are combined and the organic solvent is removed by evaporation in vacuo, whereupon the nanosol forms.

The product is then lyophilized. The powder is obtained is filled into opaque hard gelatin capsules having a content of 25 mg of indometacin in each case.

In a dissolution test according to USP (750 ml test volume, consisting of 1 part by volume of phosphate buffer pH 7.2 and 4 parts by volume of water, rotating basket, 100 rpm, 37° C.), these capsules show a capsule disintegration within 3 min.

We claim:

1. A dosage formulation that provides for the release of nanoparticles which comprises:
   (a) an inner phase that comprises at least one nanoparticle compound having an average size ranging from 10 to 800 nanometers; and
   (b) an outer phase that comprises a compound selected from the group consisting of gelatin, collagen hydrolyzates and mixtures thereof;
   wherein said inner phase is negatively charged and said outer phase is positively charged when the dosage formulation is dissolved in an aqueous solution having a pH of less than 9.5 or said inner phase is positively charged and said outer phase is negatively charged when said dosage formulation is dissolved in an aqueous solution having a pH of higher than 3.5.

2. The dosage formulation of claim 1, wherein said nanoparticle is a pharmaceutical compound.

3. The dosage formulation of claim 2, wherein the aqueous solubility of said pharmaceutical compound is less than 5 g/l at room temperature.

4. The dosage formulation of claim 1, wherein said nanoparticle has an average particle size of less than 400 nanometers.

5. The dosage formulation of claim 1, wherein said nanoparticle has an average particle size ranging from 10 to 100 nanometers.

6. The dosage formulation of claim 1, wherein the outer phase comprises gelatin.

7. The dosage formulation of claim 1, which is a liquid, aqueous dosage formulation.

8. The dosage formulation of claim 1, which is a solid dosage formulation.

9. The dosage formulation of claim 1, wherein the outer phase comprises gelatin and further comprises polyvinylpyrrolidine and the weight ratio of gelatin to polyvinylpyrrolidine ranges from 5:1 to 500:1.

10. The dosage formulation of claim 1, wherein said at least one nanoparticle compound contained is in the form of a solid powder and said powder is contained in a hard gelatin capsule.

11. The dosage formulation of claim 1, which is an immediate release medicament.

12. The dosage formulation of claim 11, which is suitable for the treatment of diabetes and wherein said nanoparticle compound comprises glibenclamide.

13. The dosage formulation of claim 11, which further comprises at least one pharmaceutical excipient or auxiliary.

14. The dosage formulation of claim 12, which further comprises at least one pharmaceutical excipient or auxiliary.

15. The dosage formulation of claim 1, wherein said gelatin comprises a bloom value ranging from 0 to 240.

16. The dosage formulation of claim 15, wherein said gelatin comprises a bloom value ranging from 0 to 170.

17. The dosage formulation of claim 1, wherein said gelatin has a maximum average molecular weight of $10^5$ daltons.

18. The dosage formulation of claim 1, wherein said gelatin has a peptide content ranging from 50 to 90%.

19. The dosage formulation of claim 1, wherein said gelatin has an average maximum molecular weight distribution ranging from $10^4$ to $9.5 \times 10^4$ daltons.

20. The dosage formulation of claim 1, wherein the outer phase comprises gelatin and the weight ratio of gelatin to said at least one nanoparticle compound ranges from 1:1 to 200:1.

21. The dosage formulation of claim 1, which comprises an immediate-release formulation and a sustained-release formulation.

22. The dosage formulation of claim 1, wherein said at least one nanoparticle compound comprises indomethacin.

23. The dosage formulation of claim 1, wherein said at least one nanoparticle compound comprises acemetacin.

24. The dosage formulation of claim 1, wherein said gelatin has a dextrorotatory amino acid content which is less than 20%.

25. The dosage formulation of claim 1, which comprises a hard gelatin capsule containing powder and a tablet wherein the powder has a more rapid dissolution rate when dissolved in an aqueous solution than the tablet.

26. The dosage formulation of claim 10, wherein said at least one nanoparticle compound contained in said inner phase has an average particle size of less than 400 nanoparticles.

27. The dosage formulation of claim 1, wherein the charge of said outer phase neutralizes the charge of said inner phase.

28. The dosage formulation of claim 1, wherein said outer phase further comprises a liquid or dried pharmaceutical auxiliary.

29. The dosage formulation of claim 28, wherein the ratio of said auxiliary to said gelatin, collagen hydrolyzate or mixture ranges from 5:1 to 500:1.

30. The dosage formulation of claim 29, wherein said weight ratio ranges from 5:1 to 30:1.

31. The dosage formulation of claim 1 which is suitable for pharmaceutical administration.

* * * * *